Figure 1:
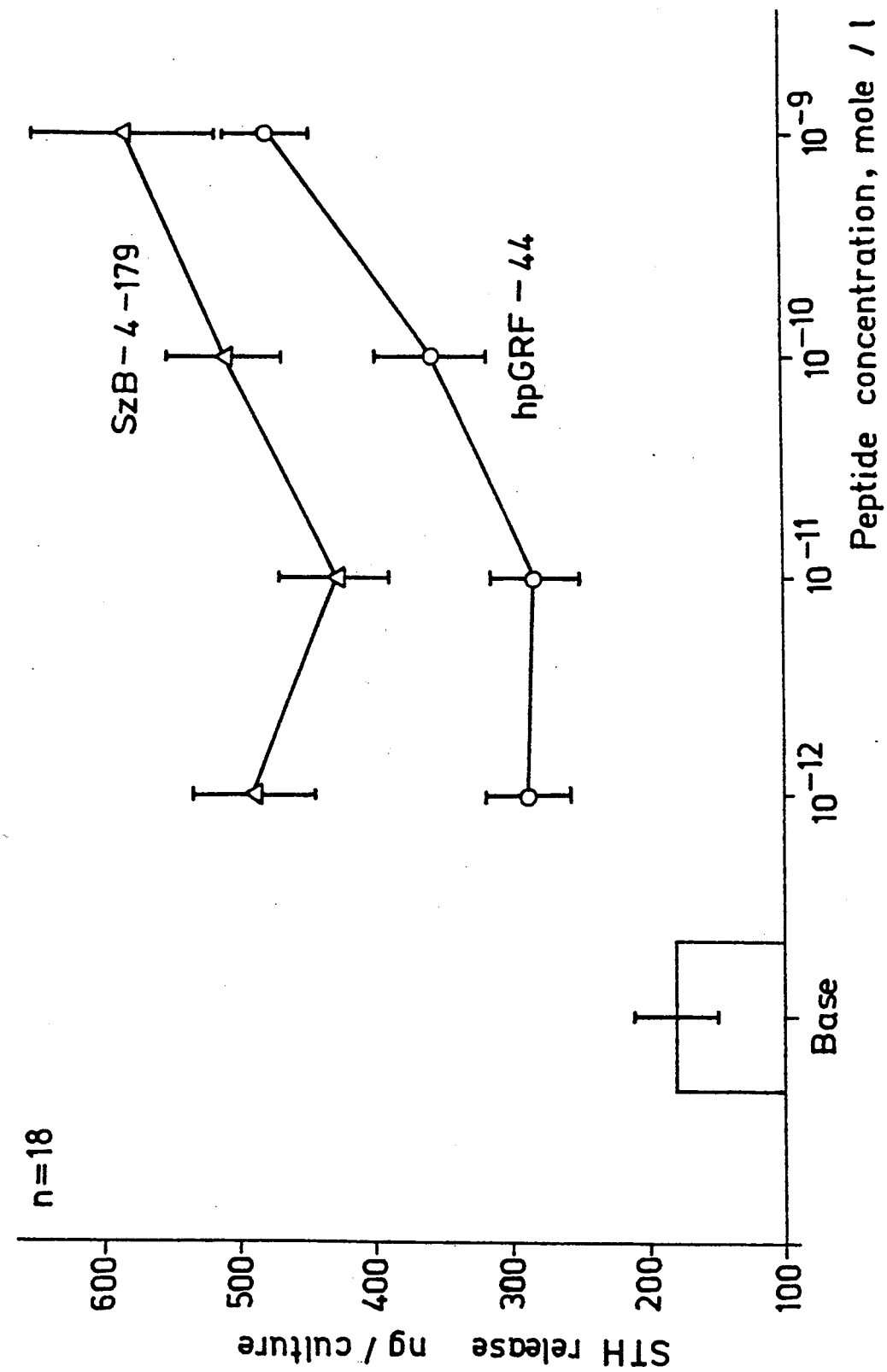

United States Patent [19]

Kovacs et al.

[11] Patent Number: 5,023,322

[45] Date of Patent: Jun. 11, 1991

[54] ANALOGS OF GROWTH HORMONE RELEASING FACTOR (GRF) AND A METHOD FOR THE PREPARATION THEREOF

[75] Inventors: Magdolna Kovacs; Judit Horváth; Sándor Vigh, all of Pécs; Imre Mezo, Budapest; István Teplán, Budapest; Balázs Szóke, Budapest; János Seprõdi, Budapest; Zsolt Vadász, Budapest; Edit Hegedüs, Budapest; Gábor Makara, Budapest; György Rappay, Budapest, all of Hungary

[73] Assignee: MTA Kutatas-es Szervezetelemzo Intezete, Budapest, Hungary

[21] Appl. No.: 400,587

[22] Filed: Aug. 30, 1989

[30] Foreign Application Priority Data

Aug. 31, 1988 [HU] Hungary .................. 4498/88
Jul. 19, 1989 [HU] Hungary .................. 3660/89

[51] Int. Cl.$^5$ .............................................. C07K 7/10
[52] U.S. Cl. .................................. 530/324; 530/399
[58] Field of Search ................ 530/324, 399; 514/12

[56] References Cited

U.S. PATENT DOCUMENTS 4,518,586 5/1985 Rivier et al. .................. 514/12
4,528,190 7/1985 Vale et al. .................. 514/12
4,801,456 1/1989 Dmengler .................. 530/324

FOREIGN PATENT DOCUMENTS 0177819 4/1986 European Pat. Off. .................. 514/12

OTHER PUBLICATIONS

Nature, 300, pp. 276-278 (1982).
Science, 218, pp. 585-587 (1982).

Peptides (ed.: D. Theodoropoulos), N.Y., pp. 481-483 (1987).
Proceedings of the Ninth Am. Peptide Symposium, Pierce Chem. Co., Rockford, Ill., pp. 707-710 (1985).
Biochemical and Biophysical Research Communications, 123 (2), pp. 854-861 (1984).
J. Med. Chem., 28, pp. 181-185 (1985).
Peptides, 7, Suppl. 1, pp. 49-52 (1986).
J. Dairy Science, 70, pp. 2511-2517 (1987).
J. Dairy Science, 71, pp. 92-100 (1988).
Nature, 300 (11/18/82), 276-278, Rivier et al.

Primary Examiner—John Doll
Assistant Examiner—T. D. Wessendorf
Attorney, Agent, or Firm—Keil & Weinkauf

[57] ABSTRACT

The invention relates to new peptides of the formula

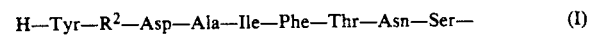
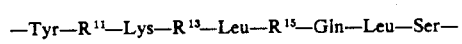
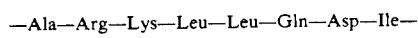
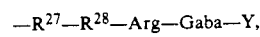

wherein
$R^2$ represents Ala or D-Ala,
$R^{11}$ represents Arg or D-Arg,
$R^{13}$ represents Val or Ile,
$R^{15}$ represents Gly, Leu, Phe or a valence bond,
$R^{27}$ represents Met or Nle,
$R^{28}$ represents Ser, D-Ser or Asn, and
Y represents OH or $NH_2$, and to salts thereof. These compounds stimulate the release of growth hormone and can be used in the therapy as well as for veterinary or animal husbandry purposes.

8 Claims, 1 Drawing Sheet

ANALOGS OF GROWTH HORMONE RELEASING FACTOR (GRF) AND A METHOD FOR THE PREPARATION THEREOF

The invention relates to new analogs of growth hormone releasing factor (GRF), furthermore to pharmaceutical compositions and to compositions for use in animal husbandry and veterinary comprising these new compounds as active agents. The invention also relates to a method for the preparation of new analogs of GRF.

Growth hormone releasing factors and analogs thereof have an important role in therapeutics and veterinary as well as in animal husbandry. In human therapy they are utilized in the treatment of disorders connected with growth hormone deficiencies and decreased growth hormone release, whereas in veterinary and animal husbandry they are applied primarily to stimulate growth, to increase fodder utilization, to improve meat/fat ratio and to increase milk production.

After the isolation of native human GRF (further on: hGRF) [Nature 300, 276 (1982); Science 218, 585 (1982)] research work has soon started to elucidate the relationships between chemical structure and biological activity. It has been found that the amino acid sequence of hGRF, a peptide of 44 residues, is very similar to those of GRFs isolated from the organisms of other mammals, such as swine, cattle and sheep. Generally the fragments from residue 3 to residue 21 appear to be the biologically active centres of the molecules concerned. The biological activity of shorter peptide fragments is generally lower than that of the native hormone. Research works [Nature 300, 276 (1982); J. Med. Chem. 30, 219 (1987); Peptides, p. 481 (ed.: D. Theodoropoulos, issued by Walter de Gruyter, Berlin, N.Y., 1988); Proceedings of the Ninth Am. Peptide Symposium (issued by Pierce Chem. Co., Rockford, Ill., 1985) p. 707; Biochem. Biophys. Res. Commun. 123, 854 (1984)] have shown, however, that even hGRF(1-29)—$NH_2$, i.e. the fragment of the native human peptide amide extending from the N-terminal through residue 29, shows favourable activity compared to the native hGRF(1-44)—$NH_2$. Tests performed with analogs of hGRF(1-29)—$NH_2$ have shown that with respect to biological activity the N-terminal part is more decisive than the C-terminal one, furthermore that the peptides are generally less active than the peptide amides [J. Med. Chem. 28, 181 (1985)]. It has also been found that the biological activity of peptides with less residues than the natural one can be modified favourably by performing certain amino acid substitutions in the peptide chain. Thus, for example, upon introducing D-Ala as residue 2 and Leu as residue 15, analogs with increased biological activity or biological half life time are obtained [J. Med. Chem. 28, 181 (1985)]. It has been observed that when replacing the residues close to the N-terminal, or generally residues 1 through 11, by the respective D isomers the biological activity generally increases.

From the references cited above and from the work of D. Coy et al. [Peptides 7, Suppl. 1, 49–52 (1986)] it follows as well that residue 27 of the natural hormone, which is the easily oxidizable methionine, can be replaced by norleucine (the structurally most related amino acid) without the loss of biological activity.

From the aspects of practical application it is a general observation that a GRF analog is active when it contains at least 29 residues. According to U.S. Pat. Nos. 4,518,586 and 4,528,190 this holds not only for GRF of human origin but also to those originating from other mammals.

From the above publications it is also known that in GRFs of human and porcine origin the sequences of the first 29 amino acids are the same. GRFs of bovine and caprin origin differ from hGRF in that they have ASP instead of Ser as residue 28. The sequence of the first 29 amino acids in ovine GRF is similar to that of the bovine and caprin hormones with the difference that it contains isoleucine as residue 13 instead of valine. It has been shown that in spite of the structural differences between the human and bovine hormones, the milk production of cattles can be influenced favourably from both quality and quantity aspects when treating them with human GRF(1-44)—$NH_2$ or human GRF(1-29)—$NH_2$ [J. Dairy Science 70, 2511 (1987) and 71, 92 (1988)].

The invention aims at providing GRF analogs which, with respect to their activity, are at least equal to but in most instances superior to the natural hormones or their fragments from the N-terminal to residue 29.

The invention is based on the recognition that GRF fragments of 30 amino acid residues which contain as residue 30 γ-aminobutyric acid or γ-aminobutyric acid amide instead of glutamine and in which the sequence of residues 1 to 29 is either the same as that of the natural hormone or comprises certain known or new amino acid substitutions are highly superior in activity to the respective natural GRFs or GRF(1-29)—$NH_2$ and GRF(1-29)—OH fragments.

In the specification the nomenclature used to define the amino acids is that specified by IUPAC-IVB Biochemical Nomenclature [J. Biol. Chem. 247, 977 (1972)]. The amino acid residue is the L-form unless otherwise expressly indicated. The meanings of the further abbreviations are as follows:

Gaba: γ-aminobutyric acid residue
Boc: tert.-butoxycarbonyl group
BHA: benzhydrylamino group
TFA: trifluoroacetic acid
DIC: diisopropyl carbodiimide
HOBt: 1-hydroxy-benzotriazole
HF: hydrogen fluoride
MPLC: medium pressure liquid chromatography
HPLC: high performance liquid chromatography
TLC: thin layer chromatography
hGRF: native GRF originating from human hypophysis (a peptide with 44 residues)
hpGRF-44: GRF isolated from human pancreatic tumor having the same amino acid composition as GRF of hypophysis origin
bGRF: native GRF originating from bovine hypophysis (a peptide with 44 residues; the sequence of residues 1 to 29 is identical with that of residues 1 to 29 of the caprin hormone)
oGRF: native GRF originating from ovine hypophysis (a peptide with 44 residues)
GH: growth hormone
STH release: release of growth hormone The invention relates to a new peptide of the formula

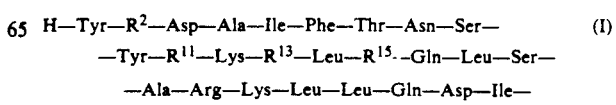

-continued $$-R^{27}-R^{28}-Arg-Gaba-Y,$$

wherein
$R^2$ represents Ala or D-Ala,
$R^{11}$ represents Arg or D-Arg,
$R^{13}$ represents Val or Ile,
$R^{15}$ represents Gly, Leu, Phe or a valence bond,
$R^{27}$ represents Met or Nle,
$R^{28}$ represents Ser, D-Ser or Asn, and
Y represents OH or $NH_2$,
or to a salt thereof.

Preferred subgroups of the peptides of formula (I) are as follows:

(1) Compounds of formula (I) wherein $R^{13}$ is Val, $R^{15}$ is Gly or Leu, $R^{28}$ is Ser, and $R^2$, $R^{11}$, $R^{27}$ and Y are as defined above. These compounds are analogs of human and porcine GRFs.

(2) Compounds of formula (I) wherein $R^2$ is Ala, $R^{11}$ is Arg, $R^{13}$ is Val, $R^{15}$ is Gly, $R^{27}$ is Met or Nle, $R^{28}$ is Asn and Y is as defined above. These compounds are analogs of bovine and caprin GRFs.

(3) Compounds of formula (I) wherein $R^2$ is Ala, $R^{11}$ is Arg, $R^{13}$ is Ile, $R^{15}$ is Gly, $R^{27}$ is Met or Nle, $R^{28}$ is Asn and Y is as defined above. These compounds are analogs of ovine GRF.

Particularly preferred members of subgroup (1) are compounds of formula (I) wherein $R^2$ is Ala, $R^{11}$ is Arg, $R^{13}$ is Val, $R^{15}$ is Gly, $R^{27}$ is Nle, $R^{28}$ is Ser and Y is as defined above.

The invention also relates to a method for the preparation of a peptide of formula (I) or a salt thereof. According to the invention the appropriately protected amino acids or amino acid fragments are coupled to one another in the appropriate sequence by a method known in peptide chemistry, then any protecting group present is split off and, if desired, a resulting peptide is converted into its salt or a resulting salt is converted into a free peptide or into another salt.

Any suitable method known in peptide chemistry can be applied to prepare the compounds of formula (I). These compounds can be prepared in liquid phase by amino acid condensation or, more preferably, by fragment condensation. According to a particularly preferred method the compounds of formula (I) are prepared by solid-phase synthesis. In this latter instance the appropriately protected Gaba is coupled first to the resin, and then the other amino acids or amino acid fragments are coupled to Gaba in the desired sequence. The amino acids or amino acid fragments are utilized in appropriately protected forms; the protecting groups are removed generally in the final step of the synthesis.

The new compounds of the invention can be applied in human therapy and in animal husbandry to stimulate the release of growth hormone. For this purpose the compounds are converted into pharmaceutical compositions or into compositions usable in veterinary or in animal husbandry.

Thus, the invention also relates to a pharmaceutical composition for stimulating the release of growth hormone. Such a composition is prepared according to the invention by admixing a compound of formula (I) or a pharmaceutically acceptable salt or metal complex thereof with a conventional pharmaceutical additive and processing it into a suitable composition by conventional pharmacotechnological methods.

Furthermore, the invention relates to a composition for use in animal husbandry or in veterinary, comprising a compound of formula (I) or a veterinarily acceptable salt or metal complex thereof as active agent together with one or more additives usable in animal husbandry or in veterinary.

The compositions defined above may contain as salts of the compounds of formula (I) acid addition salts, such as hydrochlorides, hydrobromides, sulfates, phosphates, maleates, acetates or citrates. The metal complexes of the compounds of formula (I) may be e.g. complexes formed with zinc or iron.

The pharmaceutical compositions and the compositions for use in veterinary or in animal husbandry may be e.g. compositions for intravenous, intramuscular, subcutaneous, intranasal and oral administration.

Compositions for oral administration may be e.g. tablets which may comprise as additives a carrier (such as calcium carbonate), a binding agent (such as tragacanth, maize starch or gelatine), a disintegrating agent (such as alginic acid) and/or a lubricant (such as magnesium stearate). The liquid compositions for oral administration may also comprise a flavouring agent. Typical forms of compositions for oral administration usable in animal husbandry are fodder premixes.

Compositions for parenteral administration may comprise as additive a liquid carrier for injection purposes, such as isotonic saline solution or a phosphate buffer.

The active agents may also be converted into compositions of prolonged activity e.g. by embedding the active agent into a known polymer ensuring sustained release.

The daily dose of the active agents depends on numerous factors, such as on the species of the animal to be treated, on the manner of administration and on the effect to be attained. The daily dose varies generally between 1 and 100 µg/kg body weight.

The biological effects of the compounds according to the invention were tested under in vitro and in vivo conditions. In both instances the growth hormone release was measured as a function of the concentration of the compound administered. The amount of growth hormone released was detected by radioimmune assay with a reliability limit of 95%. The results obtained were compared to those obtained when administering native hpGRF or hGRF(1-29)—$NH_2$, respectively.

TESTS PERFORMED UNDER IN VITRO CONDITIONS

The tests were performed on rat hypophysis monolayer cell culture. The results of 18 parallel tests are shown in FIG. 1, wherein the activity of $Nle^{27}$, $Gaba^{3O}$—hGRF(1-30)—$NH_2$ (marked by code SzB-4-179) was compared to that of hpGRF-44. Growth hormone release was represented as a function of the concentration of the peptide administered. The "basal value" corresponds to the natural growth hormone release of the cells. As it appears from the diagram, hpGRF-44 had to be utilized in an about fiftyfold concentration to reach the same value of STH release ng/culture, which means that the compound according to the invention was about fifty times more active than the native hormone.

TESTS PERFORMED UNDER IN VIVO CONDITIONS:

Mature male Wistar Amsterdam rats, weighing 250–300 g, were anaesthetized intraperitoneally with 60 mg/kg of pentobarbital. The peptides to be tested were dissolved in 0.9% by weight aqueous saline solution, and were administered to the animals 20 minutes after anaesthesy as an intravenous (i.v.), intramuscular (i.m.) or subcutaneous (s.c.) injection. Blood samples were taken from the jugular vein of the animals prior to the administration of the active agent ($-1$ minute) and 5, 15 and 30 minutes after challenge. The amount of growth hormone released was measured by radioimmune assay.

The tests were performed with the following compounds of formula (I):

Compound 1: D-Ala$^2$,Nle$^{27}$,Gaba$^{30}$—hGRF(1-30)—NH$_2$

Compound 2: D-Ala$^2$,Leu$^{15}$,Nle$^{27}$,Gaba$^{30}$—hGRF-(1-30)—NH$_2$

Compound 3: D-Ala$^2$,D-Arg$^{11}$,Leu$^{15}$,Nle$^{27}$,Gaba$^{30}$—hGRF(1-30)—NH$_2$ Compound 4: Nle$^{27}$,Gaba$^{30}$—hGRF(1-30)—NH$_2$ hGRF(1-29)—NH$_2$ was applied as standard.

The results are summarized in Tables I to III. In the Tables the percentage increase in activity is also indicated.

hGRF(1-29)—NH$_2$, when administered intravenously, stimulated the release of growth hormone. Therefore, when the compounds were administered intravenously, the percentage increase in activity was calculated by relating the amount of growth hormone released upon administering a compound of the invention to the amount of growth hormone released upon administering hGRF(1-29)—NH$_2$.

However, when administered intramuscularly or subcutaneously, hGRF(1-29)—NH$_2$ was practically inactive in the doses tested. Therefore, in these tests the activity of the compounds according to the invention was characterized by the percentage increase in the plasma growth hormone level related to that originally present in the plasma (basal value).

TABLE I

| | Plasma GH level (ng/ml ± SE) after intravenous administration | | | | | | | | | |
|---|---|---|---|---|---|---|---|---|---|---|
| | Peptide administered in a dose of 0.8 μg/kg | | | | | Peptide administered in a dose of 2 μg/kg | | | | |
| Time min. | Standard | Compound 1 | Increase % | Compound 2 | Increase % | Standard | Compound 1 | Increase % | Compound 2 | Increase % |
| −1 | 80.46 ± 8.96 n = 13 | 71.64 ± 18.42 n = 11 | | 96.90 ± 18.43 n = 9 | | 125.22 ± 13.12 n = 9 | 124.29 ± 14.28 n = 7 | | 100.12 ± 11.38 n = 10 | |
| +5 | 311.00 ± 34.32 n = 15 | 535.54 ± 103.86 n = 11 | 172* | 468.92 ± 68.86 n = 9 | 151* | 1061.11 ± 165.60 n = 9 | 1801.43 ± 213.84 n = 7 | 170* | 1427.90 ± 170.45 n = 10 | 135* |
| +15 | 93.60 ± 7.54 n = 15 | 240.73 ± 63.65 n = 11 | 257* | 203.51 ± 38.10 n = 9 | 217* | 393.13 ± 64.62 n = 9 | 1177.00 ± 137.81 n = 7 | 299* | 614.38 ± 99.30 n = 10 | 156* |
| +30 | 48.73 ± 3.37 n = 15 | 74.27 ± 9.20 n = 11 | 140 | 71.49 ± 7.62 n = 9 | 140 | 109.22 ± 10.39 n = 9 | 293.00 ± 28.63 n = 7 | 268* | 133.20 ± 14.56 n = 7 | 120 |

*p < 0.01 In the Table n represents the number of animals tested.
The percentage increases obtained when administering Compound 4 in a dose of 2 μg/kg were as follows: 164% after 5 minutes, 155% after 10 minutes and 204% after 30 minutes (all of them being statistically significant; p < 0.01).

TABLE II

| | Plasma GH level (ng/ml ± SE) after intramuscular administration | | | | | | | | | | | |
|---|---|---|---|---|---|---|---|---|---|---|---|---|
| | Compound 1 | | | | Compound 2 | | | | Compound 3 | | | |
| Time min. | "A" | % | "B" | % | "A" | % | "B" | % | "A" | % | "B" | % |
| −1 | 49.60 ± 6.07 n = 9 | | 48.80 ± 5.38 n = 8 | | 62.85 ± 14.67 n = 9 | | 51.73 ± 6.07 n = 8 | | 51.80 ± 1.46 n = 5 | | 43.50 ± 13.43 n = 4 | |
| +5 | 119.40 ± 24.83 n = 5 | 238 | 242.20 ± 51.34 n = 5 | 493 | 122.09 ± 20.22 n = 9 | 193 | 658.86 ± 56.50 n = 8 | 1290 | 108.50 ± 16.42 n = 6 | 209 | 247.00 ± 27.76 n = 4 | 568 |
| +15 | 120.00 ± 14.38 n = 5 | 238 | 351.00 ± 58.17 n = 5 | 716 | 138.04 ± 26.44 n = 9 | 219 | 409.17 ± 89.49 n = 8 | 786 | 98.67 ± 18.53 n = 6 | 189 | 213.75 ± 45.77 n = 4 | 489 |
| +30 | 56.00 ± 17.30 n = 5 | 110 | 149.40 ± 63.03 n = 5 | 304 | 70.19 ± 9.13 n = 9 | 110 | 184.02 ± 32.93 n = 8 | 353 | 54.50 ± 2.63 n = 5 | 105 | 110.66 ± 28.56 n = 4 | 254 |

"A": administered in a dosis of 2 μg/kg
"B": administered in a dosis of 5 μg/kg
%: percentage increase related to the basal value (GH level measured in the −1 minute)
n: number of animals tested

TABLE III

| | Plasma GH level (ng/ml ± SE) after subcutaneous administration | | | | | | | | | |
|---|---|---|---|---|---|---|---|---|---|---|
| | Compound 1 | | | | Compound 2 | | | | Compound 3 | |
| Time min. | "A" | % | "B" | % | "A" | % | "B" | % | "A" | % |
| −1 | 68.17 ± 9.61 n = 6 | | 89.67 ± 17.63 n = 9 | | 68.57 ± 8.33 n = 7 | | 63.30 ± 7.20 n = 11 | | 63.33 ± 16.70 n = 6 | |
| +5 | 285.00 ± 68.15 n = 5 | 419 | 410.67 ± 55.22 n = 9 | 455 | 304.00 ± 45.49 n = 7 | 443 | 555.85 ± 106.57 n = 11 | 880 | 237.50 ± 33.40 n = 6 | 374 |
| +15 | 376.67 ± 78.63 | 552 | 429.22 ± 69.48 | 476 | 203.29 ± 48.89 | 294 | 438.92 ± 98.15 | 695 | 193.17 ± 42.35 | 305 |

TABLE III-continued

| Time | Plasma GH level (ng/ml ± SE) after subcutaneous administration | | | | | | | | | |
|---|---|---|---|---|---|---|---|---|---|---|
| | Compound 1 | | | | Compound 2 | | | | Compound 3 | |
| min. | "A" | % | "B" | % | "A" | % | "B" | % | "A" | % |
| +30 | n = 6<br>145.67 ±<br>34.45<br>n = 6 | 213 | n = 9<br>137.78 ±<br>30.36<br>n = 9 | 152 | n = 7<br>69.14 ±<br>9.16<br>n = 7 | 100 | n = 11<br>140.38 ±<br>29.85<br>n = 11 | 222 | n = 6<br>83.83<br>16.87<br>n = 6 | 132 |

"A": administered in a dosis of 5 μg/kg
"B": administered in a dosis of 12.5 μg/kg
%: percentage increase related to the basal value (GH level measured in the −1 minute)
n: number of animals tested The main advantages of the compounds according to the invention are as follows:

they are much more active than the respective native hormones;

Gaba is a substance occurring in living organism (e.g. in nerve tissues), thus it is not extraneous and its metabolism is fully elucidated;

Gaba is an excellent spacer in solid-phase peptide synthesis, thus when it is coupled to the polymer as the first amino acid the synthesis can be performed with good efficiency;

the substitution of Nle for Met as residue 27 is chemically advantageous from the aspects of the synthesis.

The invention is elucidated in detail by the aid of the following non-limiting Examples.

EXAMPLE 1

Preparation of $Nle^{27}, Gaba^{30}$—hGRF(1–30)—$NH_2$

The peptide is prepared on a benzhydrylamine resin (capacity: 0.65 meq/g) utilizing a Beckman 990B peptide synthetizer. The protected Boc-Gaba-OH is utilized in a threefold excess calculated for the capacity of the resin. DIC condensing agent and HOBt catalyst are applied in amounts equivalent to the protected amino acid. The coupling of Boc-Gaba-OH requires 12 hours. Thereafter the resulting resin - protected amino acid compound is subjected to ninhydrin test in order to check whether coupling is complete. The coupling of Boc-Gaba-OH is generally complete in this first step; if, however, a positive ninhydrin reaction is obtained which reflects that the resin still has free amino groups for coupling, the reaction can be completed by utilizing the symmetric anhydride method. (Based on weight increase, the capacity of the resin is 75–80% of that indicated by the manufacturer firm.)

The resulting Boc-Gaba-BHA resin is deprotected and neutralized in the usual way and then the peptide synthesis is performed step by step according to the following scheme:

| | | | |
|---|---|---|---|
| 1. washing with $CH_2Cl_2$ | | thrice | 2 minutes |
| 2. cleavage with 33% $TFA/CH_2Cl_2$ | | once | 2 minutes |
| 3. cleavage with 33% $TFA/CH_2Cl_2$ | | once | 25 minutes |
| 4. washing with $CH_2Cl_2$ | | thrice | 2 minutes |
| 5. washing with ethanol | | thrice | 2 minutes |
| 6. washing with $CHCl_3$ | | thrice | 2 minutes |
| 7. neutralizing with 10% $Et_3N/CHCl_3$ | | twice | 3 minutes |
| 8. washing with $CHCl_3$ | | twice | 2 minutes |
| 9. washing with $CH_2Cl_2$ | | thrice | 2 minutes |
| 10. adding Boc-amino acid | | — | — |
| 11. coupling with DIC | | once | 120–300 minutes |
| 12. washing with $CH_2Cl_2$ | | twice | 2 minutes |
| 13. washing with ethanol | | | |

When splitting the Boc protecting group a mixture of 0.5% of indole and 0.2% of thioanisole or a mixture of 1% of anisole and 0.5% of diethyl sulfide is applied as scavenger.

In the synthesis, 3 mmoles of Boc-amino acid (corresponding to the desired sequence), 3 mmoles of DIC coupling agent and 3 mmoles of HOBt catalyst are applied in a dichloromethane solution for 1 mmole of Boc-Gaba-BHA resin. When coupling Boc-Arg(Tos)-OH, a 1:1 v/v mixture of dimethyl formamide and dichloromethane is applied as solvent. All of the protected amino acids are coupled by the carbodiimide method with the exception of Boc-Gln and Boc-Asn; in these latter instances the p-nitrophenyl ester of the appropriate protected amino acid is applied in a threefold excess in the presence of an equivalent amount of HOBt catalyst, and the reaction is performed for 12–14 hours in the presence of a 1:1 v/v mixture of dimethyl formamide and dichloromethane. The side chains of the amino acids are protected with benzyl groups for Tyr, Ser and Thr, with 2-chloro-benzyloxycarbonyl (2-Cl-Z) group for Lys and with tosyl (Tos) group for Arg, and the carboxy groups of Glu and Asp are protected with cyclohexyl (Chx) groups.

The protecting groups of the side chains and the peptide - resin compound are cleaved with liquid HF in such a way that 0.25 mmole of the peptide-BHA resin compound is admixed with 2.5 ml of anisole comprising 10% by weight of p-cresol, 100 mg of dithiotreitol and about 20–25 ml of HF and the mixture is maintained at 0° C. for 1 hour. HF is removed under reduced pressure, and the peptide is eluted from the solid residue with 15% by weight aqueous acetic acid. The solution of the peptide in 15% by weight aqueous acetic acid is purified by gel filtration through a column filled with Sephadex G-50. The peptide is purified further by MPLC on a $C_{18}$ reverse phase silica gel column (Syncroprep RP-4, 3u), a gradient of TEAP (0.25 molar aqueous triethylammonium phosphate buffer, pH: 2.55) in acetonitrile (final composition: 40:60 v/v) applied as eluting agent. The fractions are monitored by TLC and HPLC, the fractions comprising the required product are pooled and the solvent is evaporated under reduced pressure. The residue is applied again onto a MPLC column to effect further purification and to remove the salt, and a gradient of 10% by weight aqueous acetic acid solution to a 10% by weight aqueous acetic acid solution containing 30% by volume of isopropanol is applied as eluting agent. The purity and product content of the fractions are checked as indicated above. The appropriate fractions are pooled and lyophilized to obtain the desired peptide as a solid.

The physical characteristics of the product are as follows:

TLC: $R_f = 0.40$ (adsorbent: DC Alufolien Kieselgel 60/catalogue No. 5553/, solvent: a 4:1:2 v/v/v mixture of n-butanol, acetic acid and water).

HPLC: A Vydac 218 TP 546 column was applied as adsorbent, and a mixture of 30% by weight of acetonitrile and 70% by weight of a 0.25 molar aqueous triethylammonium phosphate solution (pH 2.25) was applied as eluting agent. Detection was performed on the basis of UV absorption at 215 nm with a sensitivity of 0.1 AuFS. The ISCO (Model 2350) HPLC pumps were controlled with a IBM-XT computer according to an ISCO ChemResearch program. Isocratic elution was performed and the product was characterized by the ratio of retention time to breakthrough time (k'). k'=4.37.

EXAMPLE 2

Preparation of $Nle^{27}, Gaba^{30}$—hGRF(1-30)—OH

The peptide is synthetized as described in Example 1 with the difference that Merrifield resin (chloromethyl resin) with a capacity of 0.5-0.9 meq/g is applied. The resin is reacted with a threefold excess of Boc-Gaba cesium salt in dimethyl formamide at 50° C. for 20 hours, whereupon 0.4-0.6 mmole of Gaba/g of substituted resin is obtained.

The peptide synthesis is performed then as given in Example 1, and the resulting peptide is purified and characterized as described in Example 1.

Based on TLC and HPLC examinations, a uniform product is obtained.

EXAMPLE 3

Preparation of $D-Ala^2, Nle^{27}, Gaba^{30}$—hGRF(1-30)—NH$_2$

One proceeds as described in Example 1 with the difference that Boc-D-Ala is coupled as residue 2 instead of Boc-Ala. Based on TLC and HPLC examinations, a uniform product is obtained.
TLC: R$_f$=0.39
HPLC: k'=4.55

EXAMPLE 4

Preparation of $D-Ala^2, Leu^{15}, Nle^{27}, Gaba^{30}$—hGRF(1-30)—NH$_2$

One proceeds as described in Example 3 with the difference that Boc-Leu is coupled as residue 15 instead of Boc-Gly. The physical constants of the product are determined as described in Example 1. Based on TLC and HPLC examinations, a uniform product is obtained.
TLC: R$_f$=0.41
HPLC: k'=4.55

EXAMPLE 5

Preparation of $D-Ala^2, D-Arg^{11}, Leu^{15}, Nle^{27}, Gaba^{30}$—hGRF(1-30)—NH$_2$ One proceeds as described in Example 3 with the difference that Boc-D-Arg(Tos) is coupled as residue 11 instead of Boc-Arg(Tos), and Boc-Leu is coupled as residue 15 instead of Boc-Gly. The physical constants of the product are determined as described in Example 1. Based on TLC and HPLC examinations, a uniform product is obtained.
TLC: R$_f$=0.38
HPLC: k'=3.52

EXAMPLE 6

Preparation of $D-Ala^2, Phe^{15}, Nle^{27}, Gaba^{30}$—hGRF(1-30)—NH$_2$

One proceeds as described in Example 3 with the difference that Boc-Phe is coupled as residue 15 instead of Boc-Gly. The physical constants of the product are determined as described in Example 1. Based on TLC and HPLC examinations, a uniform product is obtained.
TLC: R$_f$=0.42
HPLC: k'=4.75

EXAMPLE 7

Preparation of $D-Ala^2, desGly^{15}, Nle^{27}, Gaba^{30}$—hGRF—(1-30)—OH

One proceeds as described in Example 2 with the difference that Boc-D-Ala is coupled as residue 2 instead of Boc-Ala, and the coupling of Boc-Gly as residue 15 is omitted. The physical constants of the product are determined as described in Example 1. Based on TLC and HPLC examinations, a uniform product is obtained.
HPLC: k'=4.40

EXAMPLE 8

Preparation of $D-Ala^2, Leu^{15}, Nle^{27}, Gaba^{30}$—hGRF—(1-30)—OH

One proceeds as described in Example 7 with the difference that Boc-Leu is coupled as residue 15. The physical constants of the product are determined as described in Example 1. Based on TLC and HPLC examinations, a uniform product is obtained.
HPLC: k'=4.60

EXAMPLE 9

Preparation of $Gaba^{30}$—bGRF(1-30)—NH$_2$

One proceeds as described in Example 1 with the difference that Boc-Met is coupled as residue 27 instead of Boc-Nle, and an activated ester of Boc-aspartic acid is coupled as residue 28 instead of Boc-Ser(Bzl). Based on TLC and HPLC examinations, a uniform product is obtained.

EXAMPLE 10

Preparation of $Nle^{27}, Gaba^{30}$—bGRF(1-30)—NH$_2$

One proceeds as described in Example 9 with the difference that Boc-Nle is coupled as residue 27 instead of Boc-Met. Based on TLC and HPLC examinations, a uniform product is obtained.

EXAMPLE 11

Preparation of $Gaba^{30}$—oGRF(1-30)—NH$_2$

One proceeds as described in Example 9 with the difference that Boc-Ile is coupled as residue 13 instead of Boc-Val. Based on TLC and HPLC examinations, a uniform product is obtained.

EXAMPLE 12

Preparation of $Nle^{27}, Gaba^{30}$—oGRF(1-30)—NH$_2$

One proceeds as described in Example 11 with the difference that Boc-Nle is coupled as residue 27 instead of Boc-Met. Based on TLC and HPLC examinations, a uniform product is obtained.

What is claim is:

1. A compound of formula (I), $$H-Tyr-R^2-Asp-Ala-Ile-Phe-Thr-Asn-Ser-$$
$$-Tyr-R^{11}-Lys-R^{13}-Leu-R^{15}-Gln-Leu-Ser-$$
$$-Ala-Arg-Lys-Leu-Leu-Gln-Asp-Ile-$$
$$-R^{27}-R^{28}-Arg-Gaba-Y \quad (I)$$

wherein
- $R^2$ is Ala or D-Ala,
- $R^{11}$ is Arg or D-Arg,
- $R^{13}$ is Val or Ile,
- $R^{15}$ is Gly, Leu, Phe or a valence bond,
- $R^{27}$ is Met or Nle,
- $R^{28}$ is Ser, D-Ser or Asn, and
- Y is OH or $NH_2$, or a salt thereof.

2. A compound of formula (I) as claimed in claim 1, wherein $R^{13}$ is Val, $R^{15}$ is Gly or Leu, $R^{28}$ is Ser, and $R^2$, $R^{11}$, $R^{27}$ and Y are as defined in claim 1, or a salt thereof.

3. A compound of formula (I) as claimed in claim 1, wherein $R^2$ is Ala, $R^{11}$ is Arg, $R^{13}$ is Val, $R^{15}$ is Gly, $R^{28}$ is Asn, and $R^{27}$ and Y are as defined in claim 1, or a salt thereof.

4. A compound of formula (I) as claimed in claim 1, wherein $R^2$ is Ala, $R^{11}$ is Arg, $R^{13}$ is Ile, $R^{15}$ is Gly, $R^{28}$ is Asn, and $R^{27}$ and Y are as defined in claim 1, or a salt thereof.

5. A compound of formula (I) as claimed in claim 1, wherein $R^2$ is Ala, $R^{11}$ is Arg, $R^{13}$ is Val, $R^{15}$ is Gly, $R^{27}$ is Nle, $R^{28}$ is Ser and Y is as defined in claim 1, or a salt thereof.

6. A pharmaceutical composition comprising as active agent an effective amount of a compound of formula (I) as defined in claim 1 or a pharmaceutically acceptable salt or metal complex thereof, together with a conventional pharmaceutical additive.

7. A compound of formula (I) as claimed in claim 1, wherein $R^2$ is D-Ala, $R^{11}$ is Arg, $R^{13}$ is Val, $R^{15}$ is Leu, $R^{27}$ is Nle, $R^{28}$ is Ser, and Y is $-NH_2$.

8. A compound of formula (I) as claimed in claim 1, wherein $R^2$ is Ala, $R^{11}$ is Arg, $R^{13}$ is Val, $R^{15}$ is Gly, $R^{27}$ is Nle, $R^{28}$ is Ser, and Y is OH.